(12) United States Patent
Saab

(10) Patent No.: US 10,576,205 B2
(45) Date of Patent: Mar. 3, 2020

(54) MULTI-CHAMBER SEQUENTIAL DELIVERY SYRINGE

(71) Applicant: Ihab Saab, Detroit, MI (US)

(72) Inventor: Ihab Saab, Detroit, MI (US)

(*) Notice: Subject to any disclaimer, the term of this patent is extended or adjusted under 35 U.S.C. 154(b) by 165 days.

(21) Appl. No.: 15/567,870

(22) PCT Filed: Apr. 21, 2016

(86) PCT No.: PCT/US2016/028723
§ 371 (c)(1),
(2) Date: Oct. 19, 2017

(87) PCT Pub. No.: WO2016/172396
PCT Pub. Date: Oct. 27, 2016

(65) Prior Publication Data
US 2018/0289893 A1 Oct. 11, 2018

Related U.S. Application Data

(60) Provisional application No. 62/151,078, filed on Apr. 22, 2015.

(51) Int. Cl.
*A61M 5/19* (2006.01)
*A61M 5/315* (2006.01)
(Continued)

(52) U.S. Cl.
CPC .......... *A61M 5/19* (2013.01); *A61M 5/31596* (2013.01); *A61M 5/284* (2013.01);
(Continued)

(58) Field of Classification Search
CPC .... A61M 5/19; A61M 5/31596; A61M 5/502; A61M 5/284; A61M 5/5013;
(Continued)

(56) References Cited

U.S. PATENT DOCUMENTS 3,680,558 A 8/1972 Kapelowitz
4,932,941 A 6/1990 Min et al.
(Continued)

OTHER PUBLICATIONS

International Search Report for PCT/US2016/028723, Completed by the U.S. Patent and Trademark Office on Sep. 19, 2016, 4 Pages.

*Primary Examiner* — Emily L Schmidt
*Assistant Examiner* — Tiffany Legette
(74) *Attorney, Agent, or Firm* — Brooks Kushman P.C.

(57) ABSTRACT

It is known that fluids, for example, drugs, may be administered via a syringe. It is further known that in some instances, a second fluid must be administered following the administration of a first fluid in order to flush the first fluid. There are numerous reasons for why such flushing may be required and/or desirable. For example, flushing ensures that a patient has received the entirety of a dose of the first fluid (e.g., a drug), that the first fluid does not mix and/or react with a subsequently administered (third) fluid that may be incompatible with the first fluid, and/or that the infusion lines are clean and/or primed for a subsequent infusion, to cite a few examples. The present invention is a novel syringe design that houses the flushing solution as part of the syringe to streamline the fluid delivery (drug) and the flushing solution subsequently.

18 Claims, 4 Drawing Sheets

(51) Int. Cl.
   *A61M 5/178*   (2006.01)
   *A61M 5/28*    (2006.01)
   *A61M 5/50*    (2006.01)
   *A61M 5/31*    (2006.01)

(52) U.S. Cl.
   CPC ..... *A61M 5/502* (2013.01); *A61M 2005/1787* (2013.01); *A61M 2005/3128* (2013.01); *A61M 2005/31506* (2013.01); *A61M 2005/31598* (2013.01)

(58) Field of Classification Search
   CPC ........ A61M 5/5033; A61M 2005/3128; A61M 2005/1787; A61M 2005/31598; A61M 2005/31596
   See application file for complete search history.

(56) References Cited

U.S. PATENT DOCUMENTS

| | | | | |
|---|---|---|---|---|
| 5,259,840 | A | * | 11/1993 | Boris ................. A61M 5/3213 604/110 |
| 6,149,628 | A | * | 11/2000 | Szapiro ............. A61M 5/31596 604/191 |
| 6,602,223 | B2 | * | 8/2003 | Szapiro ................. A61M 5/284 604/82 |
| 2005/0171506 | A1 | * | 8/2005 | Hallahan ................. A61D 1/02 604/514 |
| 2008/0319400 | A1 | | 12/2008 | Thorne, Jr. et al. |
| 2012/0265171 | A1 | | 10/2012 | Thorne, Jr. et al. |
| 2013/0116657 | A1 | | 5/2013 | Hallahan et al. |

\* cited by examiner

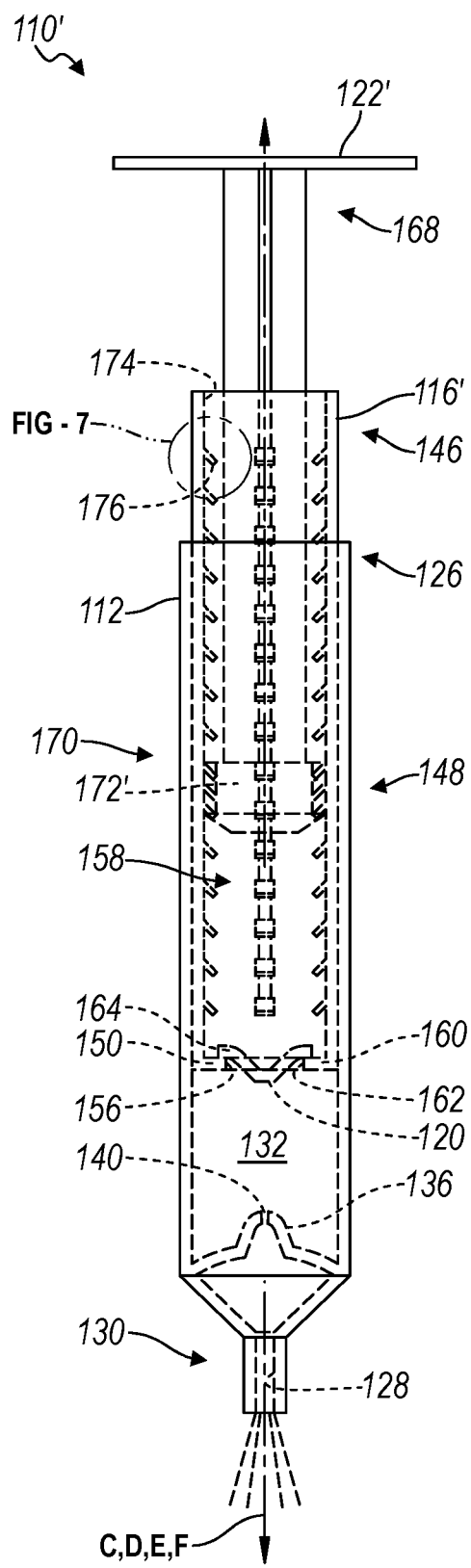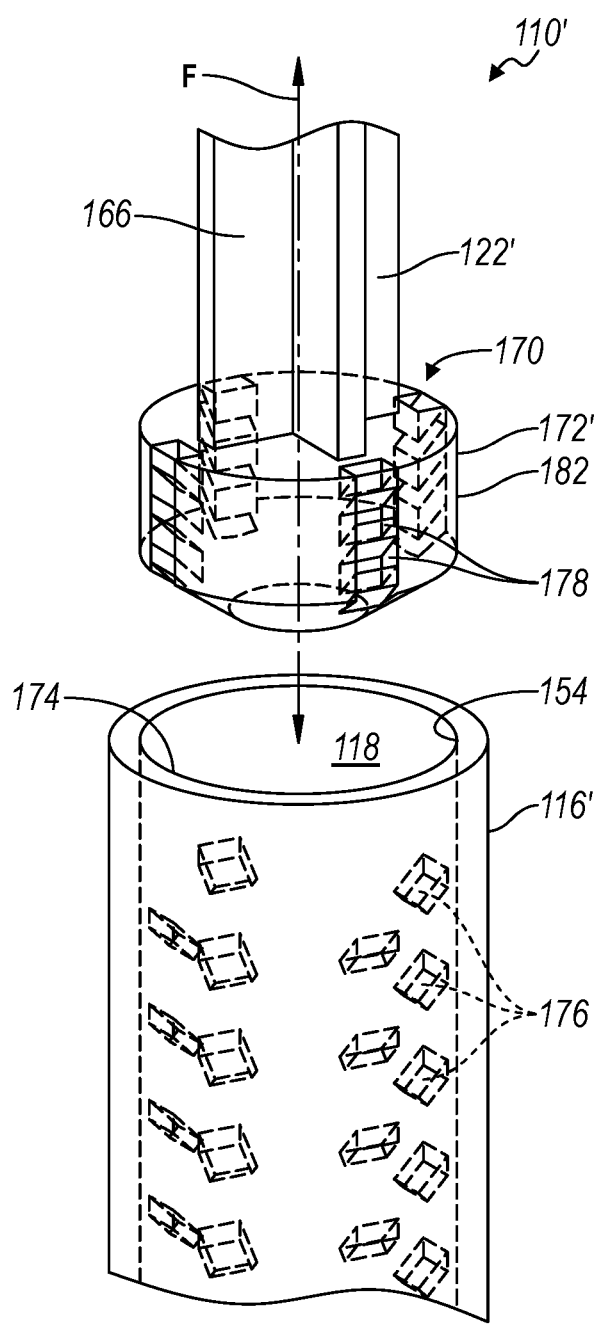
FIG. 5
FIG. 6

MULTI-CHAMBER SEQUENTIAL DELIVERY SYRINGE

CROSS-REFERENCE TO RELATED APPLICATION

This application is the U.S. national phase of PCT Application No. PCT/US2016/028723 filed on Apr. 21, 2016, which claims the benefit of U.S. Provisional Patent Application No. 62/151,078 filed on Apr. 22, 2015, the disclosures of which are incorporated in their entirety by reference herein.

TECHNICAL FIELD

The present invention is generally related to syringes and, more particularly, to multi-chamber, sequential delivery syringes.

BACKGROUND

It is known that fluids, for example, drugs, may be administered via a syringe. It is further known that in some instances, a second fluid must be administered following the administration of a first fluid in order to flush the first fluid. There are numerous reasons for why such flushing may be required and/or desirable. For example, flushing ensures that a patient has received the entirety of a dose of the first fluid (e.g., a drug), that the first fluid does not mix and/or react with a subsequently administered (third) fluid that may be incompatible with the first fluid, and/or that the infusion lines are clean and/or primed for a subsequent infusion, to cite a few examples.

The flushing of a first fluid with a second fluid may be accomplished in a number of ways. One way is by using two separate syringes, one for each fluid to be administered. Another way is by using a multi-chamber, sequential delivery syringe. In general, this type of syringe includes two or more chambers each containing a different type of fluid (e.g., a drug and a flushing fluid). The different chambers are sealed from each other such that the respective fluids therein do not mix, and the fluid in a proximal chamber is not administered or dispensed from the syringe until most, if not all, of the fluid in a distal chamber has been administered or dispensed from the syringe.

BRIEF DESCRIPTION OF THE DRAWINGS

One or more embodiments of the invention will hereinafter be described in conjunction with the appended drawings, wherein like designations denote the same or similar elements, and wherein:

FIG. 5 is a diagrammatic and elevation view of yet another illustrative embodiment of a multi-chamber, sequential delivery syringe in a first state wherein fluid in a distal chamber of the syringe is being dispensed from the syringe;

FIG. 6 is an isometric and exploded view of a portion of the syringe illustrated in FIG. 5;

DETAILED DESCRIPTION OF ILLUSTRATED EMBODIMENT(S)

The description below pertains to a multi-chamber, sequential-delivery syringe that may used to administer a first fluid (e.g., a drug in liquid form) contained in a distal chamber of the syringe (i.e., the chamber closest to the needle or outlet of the syringe), and to then subsequently administer a second fluid (e.g., a flushing liquid, such as, for example, saline) contained in a proximal chamber of the syringe (i.e., the chamber furthest away from the needle or outlet of the syringe) once most, if not all, of the first fluid has been dispensed from the syringe. It will be appreciated that while the description below is primarily with respect to an embodiment wherein the syringe includes two chambers, in other embodiments, the syringe may include more than two chambers. Accordingly, the present disclosure is not intended to be limited to the syringe having any particular number of chambers.

In an embodiment, the syringe is a pre-loaded or pre-packaged syringe wherein the chambers of the syringe are filled by the manufacturer or another party prior to the syringe being distributed to a customer (e.g., physician, hospital, or other healthcare professional). For example, a proximal chamber of the syringe may be prefilled with a flushing fluid (e.g., a flushing liquid such as saline) and a distal chamber of the syringe may be prefilled with a drug or other medication that is administered to the patient before the flushing fluid. In other embodiments, however, the syringe may not be pre-loaded, or may be only partially pre-loaded, such that at least one chamber of the syringe is initially empty and may be filled by a healthcare professional in the field (i.e., at least one of the chambers is fillable). For example, a proximal chamber of the syringe may be prefilled with a flushing fluid (e.g., a flushing liquid such as saline) and a distal chamber may be empty so that a user (e.g., healthcare professional) may fill it with a fluid (e.g., a drug in liquid form) of their choosing (e.g., the user may aspirate the fluid of their choosing into the distal chamber). Accordingly, the present disclosure is not intended to be limited to any particular type(s) of multi-chamber, sequential delivery syringes (e.g., pre-loaded, partially pre-loaded, or unloaded), but rather the disclosure may find application with any number of type(s) of syringes.

Figure 1:
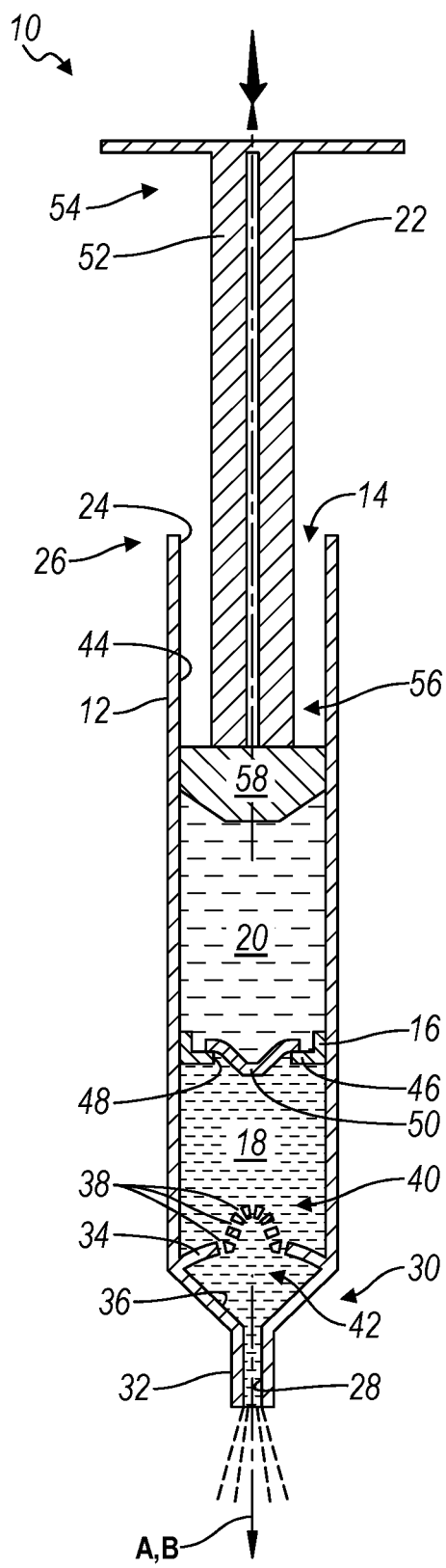
FIG. 1 is a diagrammatic and elevation view of an illustrative embodiment of a multi-chamber, sequential delivery syringe in a first state wherein fluid in a distal chamber of the syringe is being dispensed from the syringe.
Figure 2:
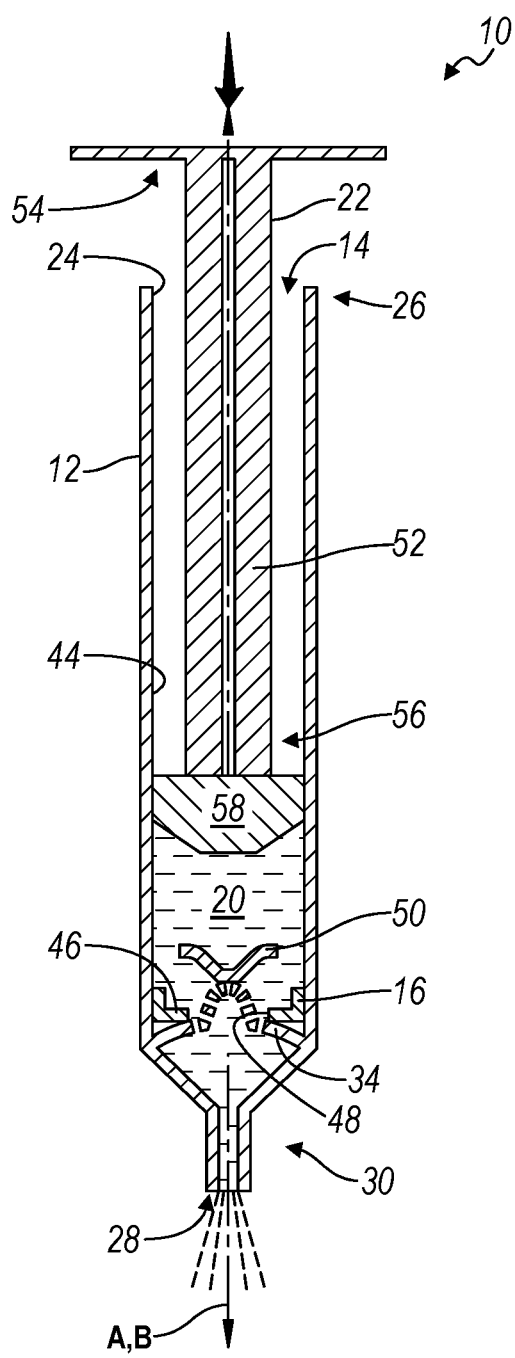
FIG. 2 is a diagrammatic and elevation view of the syringe illustrated in FIG. 1 in a second state wherein fluid in a proximal chamber of the syringe is being dispensed from the syringe.

With reference to FIGS. 1 and 2, there is shown a diagrammatic representation of an embodiment of a syringe 10 that, in at least some embodiments, comprises a pre-loaded syringe. In this embodiment, the syringe 10 comprises: an elongate hollow barrel 12 having an interior space 14; a valve 16 carried by the barrel 12 and disposed within the interior space 14 thereof, and that divides the interior space 14 of the barrel 12 into a first (or distal) chamber 18 and a second (or proximal) chamber 20; and a plunger 22 that, when the syringe 10 is assembled, is carried by the barrel 12 and at least partially disposed within the interior space 14 thereof. In at least some embodiments, the syringe 10 may further include a needle (not shown).

The barrel 12 has an opening 24 at a proximal end 26 thereof that provides access into the interior space 14 of the barrel 12, and that is sized and shaped to receive the plunger 22. The barrel further includes an orifice or passageway 28 at a distal end 30 thereof through which fluid in the chambers 18, 20 of the syringe may be dispensed from the syringe. The barrel 12 further includes an axis A extending through and between the proximal and distal ends 26, 30 of the barrel. As briefly mentioned above, in an embodiment, the syringe 10 may further include a hollow needle (not shown). In such an embodiment, the needle may be coupled to the barrel 12 at or near the distal end 30 thereof, and at least a portion of the needle may be disposed within, and in fluid communication with, the orifice 28. More specifically, in an embodiment, the barrel 12 may include a hub 32 through which the orifice 28 extends and that functions to couple the needle to the barrel 12 and to lock the needle in place.

As shown in FIG. 1, the barrel 12 further includes one or more knobs or other protruding elements or protuberances 34 disposed and carried within the interior space 14 of the barrel 12 proximate (i.e., at or near) the distal end 30 thereof. More specifically, the knob(s) 34 are disposed and carried within the distal chamber 18 of the barrel 12 and between the valve 16 and the orifice 28 when the syringe 10 is in a state in which the fluid from the distal chamber 18 has not yet been administered or dispensed from the syringe 10. For purposes of illustration, the description below will be with respect to an embodiment wherein the barrel 12 has a single knob 34, though in other embodiments, the barrel 12 may include a plurality of knobs 34, as the present disclosure is not limited to any particular number of knobs.

In an embodiment, the knob 34 may be disposed at the distal-most point 36 within the interior space 14 of the barrel 12; while in other embodiments, the knob 34 may be disposed or located somewhere between the distal-most point 36 and the valve 16. In any event, in an embodiment, the knob 34 is positioned or located at or near the distal end 30 of the barrel 12 such that most, if not all, of the fluid (e.g., liquid) in the distal chamber 18 (i.e., the chamber closest to the knob 34 and orifice 28) must be dispensed from the syringe 10 prior to, as will be described below, the valve 16 engaging the knob 34, and thus, fluid (e.g., liquid) in the proximal chamber 20 (i.e., the chamber furthest away from the knob 34 and orifice 28) being dispensed from the syringe 10. The knob 34 has a central axis B that, in an at least some embodiments such as that shown in FIGS. 1 and 2, is parallel to and coaxial with the axis A of the barrel 12, and the knob 34 extends or projects into the interior space 14 of the barrel 12 in an axial direction relative to the axis B toward the proximal end 26 of the barrel 12 (e.g., toward the opening 24). In other embodiments, however, the axis B may not be parallel to and/or may be offset from the axis A. The knob 34 may be integrally formed with the barrel 12 such that the barrel 12 and knob 34 are of a unitary (e.g., molded) construction; while in another embodiment, the knob 34 may formed separately from the barrel 12 and either directly or indirectly coupled to one or more inner surfaces of the barrel 12 using any number of suitable coupling techniques.

In addition to the above, in at least some embodiments or implementations, the knob 34 may be porous such that fluid in the syringe 10 may pass through the knob 34 to the orifice 28 where it is ultimately dispensed from the syringe 10. More particularly, in an embodiment, the knob 34 has one or more apertures or throughgoing passageways 38 therein (shown in dashed lines in FIGS. 1 and 2) that are configured to allow fluid to be communicated from one side of the knob 34 (e.g., the proximal side 40) to the other (e.g., the distal side 42). In the embodiment illustrated in FIGS. 1 and 2, the knob 34 includes a plurality of apertures 38; it will be appreciated, however, that in other embodiments, the knob 34 may include only a single aperture as the present disclosure is not intended to be limited to any particular number of apertures.

As briefly described above and as shown in FIG. 1, the valve 16 is disposed and carried within the interior space 14 of the barrel 12, and divides the interior space 14 into distal and proximal chambers 18, 20—the distal chamber 18 being located or extending between the valve 16 and the distal end 30 of the barrel 12, and the proximal chamber 20 being located or extending between the valve 16 and the plunger 22. As will be described more fully below, the valve 16 is configured slide or move within the interior space 14 of the barrel 12 as the plunger 22 moves (i.e., upon the application of a suitable amount of external force to the plunger 22 that causes fluid in the distal chamber 18 to be dispensed from the syringe 10 and the valve 16 and fluid in the proximal chamber 20 (and the proximal chamber 20 itself) to move toward the distal end 30 of the barrel 12).

When in a first condition or state, for example, that shown in FIG. 1, the valve 16 provides a fluid (e.g., liquid) seal between the distal and proximal chambers 18, 20 to prevent the fluids contained therein from mixing. Accordingly, at least a portion of the valve 16 is sufficiently elastically deformable or resilient (e.g., formed of rubber, plastic, or other like material) such that it may be compressed for insertion into the interior space 14 of the barrel 12, and then upon insertion, returns at least partially to its original form and applies a radial force or pressure against one or more interior surface(s) 44 of the barrel 12. When in a second condition or state, for example, that shown in FIG. 2, the valve 16 no longer provides a seal between the chambers 18, 20, but rather allows fluid to flow out from the proximal chamber 20.

In an embodiment, the valve 16 comprises a base portion 46 having an aperture 48 disposed therein and a plug portion 50. The aperture 48 may be arranged such that when the valve 16 is properly inserted into the barrel 12, the aperture 48 is axially aligned with the knob 34 at or near the distal end 30 of the barrel 12. The aperture 48 may also be sized and shaped so as to receive at least a portion of the knob 34 therein, as will be described in greater detail below.

When in the first condition or state described above and shown in FIG. 1, the plug 50 is disposed or carried within the aperture 48 of the base 46 so as to prevent the flow of fluid from either of the chambers 18, 20 through the aperture 48. The plug 50 may be retained within the aperture 48, and thus the valve 16 may be held together, in a number of ways. One way, though certainly not the only way, is by a suitable adhesive. An additional or alternative way is by the pressure applied to the valve 16 by the fluid(s) in one or more of the chambers 18, 20. Accordingly, it will be appreciated that the valve 16 may be held together in any suitable manner, as the present disclosure is not intended to be limited to any particular way(s) of doing so.

Conversely, when the valve 16 is in the second condition or state described above and shown in FIG. 2, the plug 50 is dislodged or disengaged from the base 46, thereby allowing for the flow of fluid through the aperture 48 in the base 46. As will be described in greater detail below, the plug 50 may be dislodged from the base 46 by the knob 34 at or near the distal end 30 of the barrel 12. In an embodiment wherein the valve 16 has the construction or form described above, the base portion 46 may comprise the elastically deformable/resilient portion of the valve that forms a seal between the chambers 18, 20. While a particular construction for the valve 16 has been described above, it will be appreciated that the present disclosure is not intended to be limited to any particular construction(s), but rather any suitable valve construction may be used.

When the syringe 10 is assembled, at least a portion of the plunger 22 is disposed and carried within the interior space 14 of the barrel 12 and is operative to cause fluid in the syringe 10 to be displaced and dispensed therefrom when it is depressed with a sufficient amount of force by a user. The plunger 22 may comprise any suitable plunger known in the art, and thus, a detailed description of the plunger 22 will not be provided. To summarize, however, the plunger 22 may comprise an elongate shaft 52 having a first end 54 and a second end 56 opposite the first end 54, and is sized such that it may be inserted into the interior space 14 of the barrel 12 through the opening 24 at the proximal end 26 of the barrel 12. The plunger 22 further includes stopper 58 at the second end 56 thereof. In embodiment, the stopper 58 provides a liquid seal to prevent fluid in the proximal chamber 20 from flowing past the stopper 58 and potentially out of the syringe 10 through the opening 24 at the proximal end 26 of the barrel 12. To that end, in an embodiment, and similar to the valve 16 described above, at least a portion of the stopper 58 is sufficiently elastically deformable or resilient (e.g., formed of rubber, plastic, or another suitable material) such that it may be compressed for insertion into the interior space 14 of the barrel 12, and then upon insertion, returns at least partially to its original form and applies a radial force or pressure against one or more interior surface(s) 44 of the barrel 12. In addition to providing a seal, the stopper 58 also serves to wipe one or more inner surface(s) 44 of the barrel 12 as the plunger 22 is depressed and moved along the length of the barrel 12 in either axial direction relative to the axis A of the barrel 12 in order to, for example, maximize the amount of fluid that is dispensed from the syringe 10.

With reference to both FIG. 1 and FIG. 2, in operation, the plunger 22 is depressed in an axial direction toward the distal end 30 of the barrel 12 (i.e., toward the fluid in the chambers 18, 20) causing the stopper 58 thereof to contact or engage the fluid in the proximal chamber 20. As the plunger 22 is urged toward the distal end 30 of the barrel 12, the pressure applied causes a number of things to happen. First, as shown in FIG. 1, the pressure or force exerted on the plunger 22 causes the plunger 22 to move within the interior space 14 of the barrel 12 in an axial direction toward the distal end 30. As the plunger 22 moves, the pressure or force applied the plunger 22 is transmitted through the fluid in the proximal chamber 20 to the valve 16 and the fluid in the distal chamber 18. This pressure/force causes the fluid contained within the distal chamber 18 to flow out of the syringe 10 through the orifice 28. Accordingly, fluid on the distal side 42 of the knob 34 flows out from the syringe through the orifice 28 and, if applicable, the needle, and fluid on the proximal side 40 of the knob 34 flows through the aperture(s) 38 in the knob 34 and then through the orifice 28 and, if applicable, the needle.

Contemporaneous with the dispensing of the fluid contained within the distal chamber 18 and the continued depressing of the plunger 22, both the proximal chamber 20 (and the fluid therein) and the valve 16 move in an axial direction toward the distal end 30 of the barrel 12. More particularly, the force applied to the plunger 22 causes the valve 16 to slide along one or more of the interior surfaces 44 of the barrel 12. As the valve 16 moves, it wipes the interior surface(s) 44 it passes over, and also allows for the proximal chamber 20 and the fluid contained therein to move along with the valve 16. As the plunger 22 is urged further toward the distal end 30, the valve 16 eventually engages the knob 34 in the barrel 12. More specifically, and with reference to FIG. 2, the valve 16 and the knob 34 are arranged such that the plug 50 of the valve 16 is axially aligned with the knob 34. As the valve 16 engages the knob 34 and continues to move toward the distal end 30, the knob 34 dislodges the plug 50 from the valve base 46, thereby opening the valve 16 and allowing at least some of the fluid in the proximal chamber 20 to flow out from the proximal chamber 20 through the aperture 48 in the valve base 46. This fluid then flows through aperture(s) 38 in the knob 34 and out of the syringe 10 through the orifice 28. As the base portion 46 continues to move toward the distal end 30 without the plug 50, it passes over at least a portion of the knob 34 (i.e., at least a portion of the knob 34 passes through the aperture 48 in the valve base 46) such that the knob 34 is now disposed within the proximal chamber 20. As a result, the remaining fluid contained in the proximal chamber 20 may then pass through the aperture(s) 38 in the knob 34 and out of the syringe 10 through the orifice 28, and, if applicable, the needle. The flow of fluid out from the proximal chamber 30 is promoted or advanced by continued force applied to the plunger 22, which urges the fluid out from the proximal chamber 20 as the plunger 22 continues to move within the interior space 14 of the barrel 12 toward the distal end 30 thereof.

It will be appreciated that in an embodiment, all of the fluid in the distal chamber 18 will have been dispensed from the syringe 10 prior to the plug 50 being dislodged from the valve base 46 and the fluid in the proximal chamber 20 being dispensed from the syringe 10 such that the fluids in the distal and proximal chambers 18, 20 do not mix. In other embodiments, most, if not all, of the fluid in the distal chamber 18 will have been dispensed from the syringe 10 prior to the plug 50 being dislodged and the fluid in the proximal chamber 20 being dispensed in order to substantially limit, if not prevent, the fluid in the proximal chamber 20 mixing with the fluid in the distal chamber 18.

Figure 3:
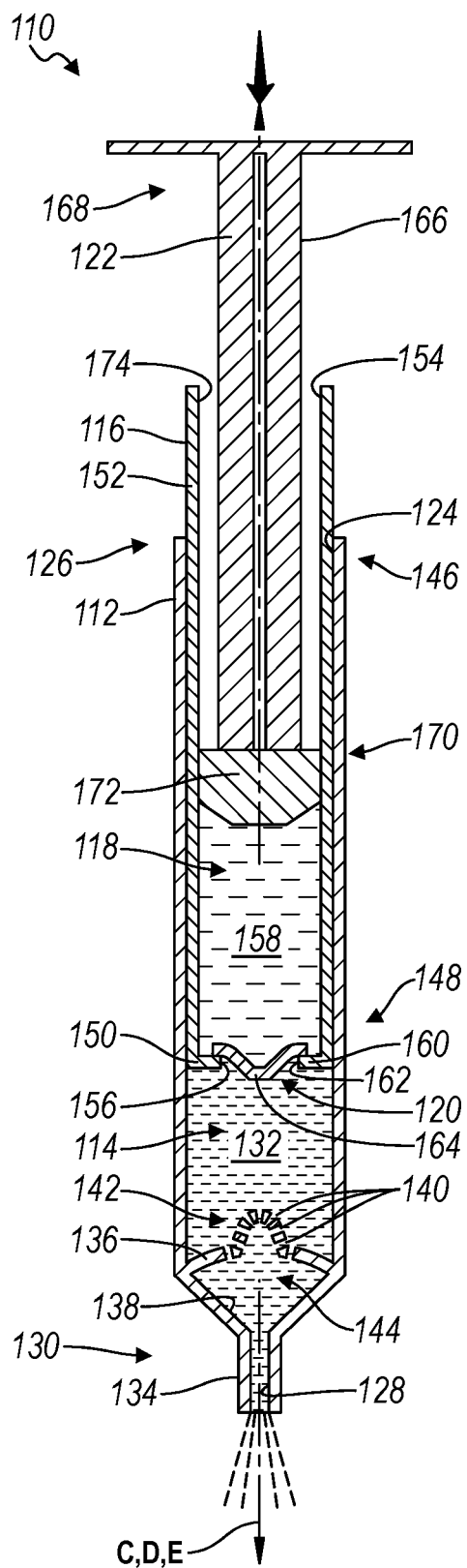
FIG. 3 is a diagrammatic and elevation view of another illustrative embodiment of a multi-chamber, sequential delivery syringe in a first state wherein fluid in a distal chamber of the syringe is being dispensed from the syringe.
Figure 4:
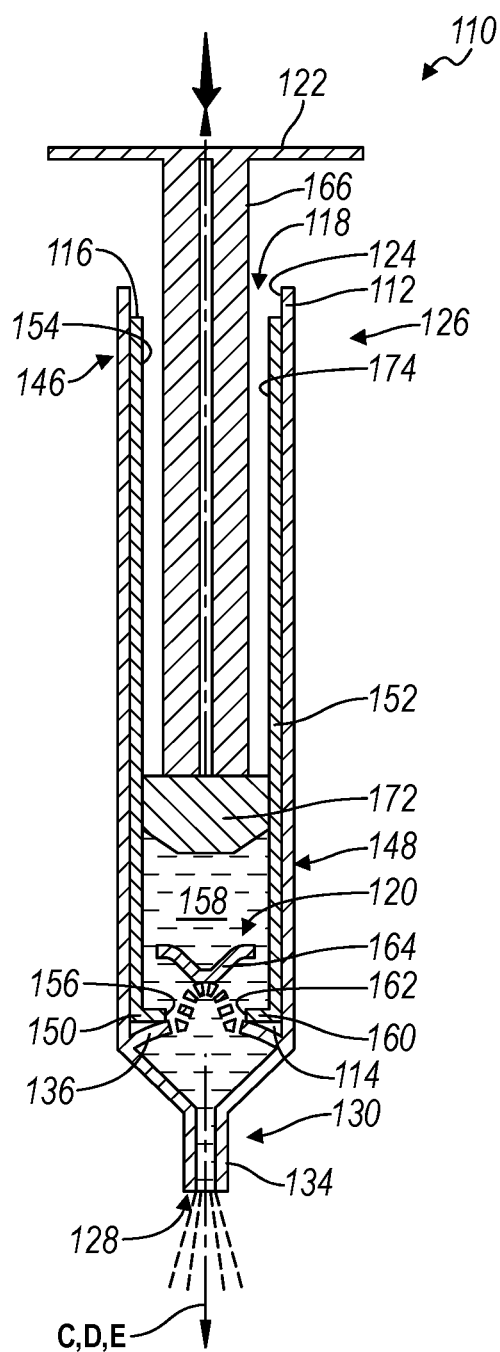
FIG. 4 is a diagrammatic and elevation view of the syringe illustrated in FIG. 3 in a second state wherein fluid in a proximal chamber of the syringe is being dispensed from the syringe.

With reference to FIGS. 3 and 4, there is shown a diagrammatic representation of another illustrative embodiment of a syringe 110 that, in at least some embodiments, comprises an entirely pre-loaded syringe, while in other embodiments, comprises a partially-loaded syringe (e.g., having a distal chamber that may be filled by a user). In this embodiment, the syringe 110 comprises: a first or outer elongate hollow barrel 112 having an interior space 114; a second or inner elongate hollow barrel 116 having an interior space 118 and a valve 120 and that, when the syringe is assembled, is carried by the first hollow barrel 112; and a plunger 122 that, when the syringe 110 is assembled, is carried by the second barrel 116. As with the embodiment described above, in at least some embodiments, the syringe 110 may further include a needle (not shown).

The first barrel 112 has an opening 124 at a proximal end 126 thereof that provides access into the interior space 114 of the barrel 112 and is sized and shaped to receive the second elongate barrel 116. The first barrel 112 further includes an orifice or passageway 128 at a distal end 130 thereof through which fluid in the syringe 110 may be dispensed from the syringe 110. As shown in FIG. 3, when the first barrel 112 is assembled with second barrel 116, at least a portion of the interior space 114 of the first barrel 112 at or near the distal end 130 thereof (e.g., between the second barrel 116 and the distal end 130 of the first barrel 112) comprises a fluid chamber 132 that, as will be described in greater detail below, constitutes or comprises a distal chamber of the syringe 110 (i.e., distal chamber 132 of the syringe 110). The barrel 112 further includes an axis C extending through and between the proximal and distal ends 126, 130 of the barrel 112. As with the embodiment illustrated in FIGS. 1 and 2, in an embodiment, the syringe 110 may further include a hollow needle (not shown). In such an embodiment, the needle may be coupled to the barrel 112 at or near the distal end 130 thereof, and at least a portion of the needle may be disposed within, and in fluid communication with, the orifice 128. More specifically, the first barrel 112 may include a hub 134 at the distal end 130 thereof through which the orifice 128 extends and that functions to couple the needle to the barrel 112 and to lock the needle in place.

As shown in FIG. 3, the first barrel 112 further includes one or more knobs or other protruding elements or protuberances 136 located and carried within the interior space 114 of the first barrel 112 proximate (e.g., at or near) the distal end 130 thereof. More specifically, in an embodiment, the knob(s) 136 are disposed within the fluid chamber (i.e., distal chamber 132) of the first barrel 112 and, when the first barrel 112 is assembled with the second barrel 116, between the valve 120 of the second barrel 116 and the orifice 128 of the first barrel 112 when the syringe 110 is in a state in which fluid contained in the distal chamber 132 has not yet been dispensed or administered. For purposes of illustration, the description below will be with respect to an embodiment wherein the first barrel 112 has a single knob 136; though it will be appreciated that in other embodiments the barrel 112 may include a plurality of knobs 136.

In an embodiment, the knob 136 may be disposed at the distal-most point 138 within the interior space 114 of the first barrel 112; while in other embodiments, the knob 136 may be disposed or located somewhere between the distal-most point 138 and the valve 120 of the second barrel 116. In any event, in an embodiment, the knob 136 is positioned or located at or near the distal end 130 of the first barrel 112 such that most, if not all, of the fluid in the distal chamber 132 must be dispensed from the syringe 110 prior to, as will be described below, the valve 120 of the second barrel 116 engaging the knob 136. As shown in FIG. 3, the knob has a central axis D that, in an at least some embodiments, is parallel to and coaxial with the axis C of the first barrel 112, and the knob 136 extends or projects into the interior space 114 of the first barrel 112 in an axial direction relative to the axis D toward the proximal end 126 of the first barrel 112 (e.g., toward the opening 124). In other embodiments, however, the axis D may not be parallel to and/or may be offset from the axis C. The knob 136 may be integrally formed with the barrel 112 such that the barrel 112 and knob 136 are of a unitary (e.g., molded) construction; while in another embodiment, the knob 136 may formed separately from the barrel 112 and either directly or indirectly coupled to one or more inner surfaces of the barrel 112 using any number of suitable coupling techniques.

As with the illustrative embodiment depicted in FIGS. 1 and 2, in at least some embodiments or implementations, the knob 136 may be porous such that fluid in the syringe 110 may pass through the knob 136 to the orifice 128 where it is ultimately dispensed from the syringe 110. More particularly, in an embodiment, the knob 136 has one or more apertures or throughgoing passageways 140 (shown in dashed lines in FIGS. 3 and 4) that are configured to allow fluid to be communicated from one side of the knob (e.g., the proximal side 142) to the other (e.g., the distal side 144). In the embodiment illustrated in FIGS. 3 and 4, the knob 136 includes a plurality of apertures 140; it will be appreciated, however, that in other embodiments, the knob 136 may include only a single aperture, as the present disclosure is not intended to be limited to any particular number of apertures.

As with the first barrel 112, the second barrel 116 has a first or proximal end 146 and a second or distal end 148 opposite the proximal end 146, and includes or defines an axis E extending between and through the proximal and distal ends 146, 148 that, when the syringe 110 is assembled, is generally coaxial with the axis C of the first barrel 112 and, in at least some implementations, the axis D of the knob 136. The second barrel 116 has a base 150 at the distal end 148 and one or more sidewalls 152 extending axially from the base 150 to the proximal end 146. The second barrel 116 has an opening 154 at the proximal end 146 that provides access into the interior space 118 of the second barrel 116 defined by the base 150 and sidewall(s) 152 thereof. The opening 154 is sized and shaped to receive the plunger 122 of the syringe 110. The second barrel 116 also includes an axially-extending aperture 156 in the base 150 thereof that, as will be described below, comprises a constituent part of the valve 120. As shown in FIG. 3, when the second barrel 116 is assembled with the plunger 122, at least a portion of the interior space 118 of the second barrel 116 proximate (e.g., at or near) the distal end 148 thereof (e.g., between the plunger 122 and the distal end 148 of the second barrel 116) comprises a fluid chamber that, as will be described in greater detail below, constitutes or comprises a proximal chamber 158 of the syringe 110.

As briefly described above and shown in FIG. 3, the second barrel 116 includes the valve 120 that in the illustrated embodiment is disposed at the distal end 148 of the barrel 116. As will be described in greater detail below, the valve 120 slides or moves along with the second barrel 116 within the interior space 118 of the first barrel 112 upon the application of a sufficient external force to the plunger 122.

When in a first condition or state, for example, that shown in FIG. 3, the valve 120 provides a fluid (e.g., liquid) seal between the fluid chambers of the first and second barrels 112, 116 (i.e., the distal and proximal fluid chambers 132, 158) of the syringe 110, respectively, to prevent the fluids contained therein from mixing. When in a second condition or state, for example, that shown in FIG. 4, the valve 120 no longer provides a seal between the fluid chambers, but rather allows fluid to flow out from the fluid chamber of the second barrel (i.e., the proximal chamber 158 of the syringe 110).

In an embodiment, the valve 120 comprises a base portion 160 having an aperture 162 disposed therein and a plug portion 164. In the embodiment illustrated in FIGS. 3 and 4, the base 150 of the second barrel 116 comprises the base 160 of the valve 120, and the aperture 156 in the base 150 comprises the aperture 162 in the valve base 160. It will be appreciated, however, that other valve arrangements are certainly possible. In any event, in the embodiment illustrated in FIGS. 3 and 4, the aperture 162 may be arranged such that when the second barrel 116 is properly inserted into the first barrel 112, the aperture 162 is axially aligned with the knob 136 at or near the distal end 130 of the first barrel 112. The aperture 162 may also be sized and shaped so as to receive at least a portion of the knob 136 therein, as will be described in greater detail below. In an embodiment, the base portion 160 of the valve 120 provides a liquid seal to prevent fluid in the fluid chamber of the first barrel 112 (i.e., the distal chamber 132 of the syringe 110) from flowing between the outer surface(s) of the second barrel 116 and the inner surface(s) of the first barrel 112 past the base 160. To that end, in an embodiment, at least a portion of the base 160 (e.g., the outer rim or annular surface) is sufficiently elastically deformable or resilient (e.g., formed of rubber, plastic, or another suitable material) such that it may be compressed for insertion into the interior space 114 of the first barrel 112, and then upon insertion, returns at least partially to its original form and applies a radial force against one or more interior surface(s) of the first barrel 112

When in the first condition or state described above and shown in FIG. 3, the plug 164 is disposed and carried within the aperture 162 of the valve base 160 so as to prevent the flow of fluid from either of the fluid chambers of the first and second barrels 112, 116 (e.g., the distal or proximal chambers 132, 158) through the aperture 162. The plug 164 may be retained within the aperture 162, and thus the valve 120 may be held together, in a number of ways. One way, though certainly not the only way, is by a suitable adhesive. An additional or alternative way is by the pressure applied to the valve 120 by the fluid(s) in one or more of the distal chamber 132 and/or proximal chamber 158 of the syringe 110. Accordingly, it will be appreciated that the valve 120 may be held together in any suitable manner as the present disclosure is not intended to be limited to any particular way(s) of doing so.

Conversely, when the valve 120 is in the second condition or state described above and shown in FIG. 4, the plug 164 is dislodged or disengaged from the valve base 160, thereby allowing for the flow of fluid through the aperture 162 in the base 160. As will be described in greater detail below, the plug 164 may be dislodged from the base 160 by the knob 136 at or near the distal end 130 of the first barrel 112. While a particular construction and arrangement for the valve 120 has been described above, it will be appreciated that the present disclosure is not intended to be limited to any particular construction(s), but rather any suitable valve construction may be used.

When the syringe 110 is assembled, at least a portion of the plunger 122 is carried within the interior space 118 of the second barrel 116 and is operative to cause fluid in the syringe 110 to be dispensed therefrom when it is depressed with a sufficient amount of force by a user. The plunger 122 may comprise any suitable plunger known in the art, and thus, a detailed description of the plunger 122 will not be provided. To summarize, however, the plunger 122 may comprise an elongate shaft 166 having a first end 168 and a second end 170 opposite the first end 168, and is sized such that it may be inserted into and the interior space 118 of the second barrel 116 through the opening 154 thereof. The plunger 122 may further include a stopper 172 at the second end 170 thereof. In embodiment, the stopper 172 provides a liquid seal to prevent fluid in the fluid chamber of the second barrel 116 (i.e., the proximal chamber 158 of the syringe 110) from flowing past the stopper 172 and potentially out of the syringe 110 through the opening 154 at the proximal end 146 of the second barrel 116. To that end, in an embodiment, at least a portion of the stopper 172 is sufficiently elastically deformable or resilient (e.g., formed of rubber, plastic, or another suitable material) such that it may be compressed for insertion into the interior space 118 of the second barrel 116, and then upon insertion, returns at least partially to its original form and applies a radial force against one or more interior surface(s) 174 of the second barrel 116. In addition to providing a seal, the stopper 172 also serves to wipe one or more interior surface(s) 174 of the second barrel 116 as the plunger 122 is depressed and moves along the length of the second barrel 116 in either axial direction relative to the axis E of the second barrel 116 in order to, for example, maximize the amount of fluid that is dispensed from the syringe 110.

With reference to FIGS. 3 and 4, in operation, the plunger 122 is depressed in an axial direction toward the distal end 148 of the second barrel 116 (i.e., toward the fluid in the fluid chamber thereof) causing the stopper 172 of the plunger 122 to contact or engage the fluid in the fluid chamber of the second barrel 116 (i.e., the proximal chamber 158). As the plunger 122 is urged further toward the distal end 148 of the second barrel 116, the pressure applied causes a number of things to happen. First, the pressure or force exerted on the plunger 122 causes the second barrel 116 to move within the interior space 114 of the first barrel 112 in an axial direction toward the distal end 130 of the first barrel 112. As a result, fluid in the fluid chamber of the first barrel 112 (i.e., the distal chamber 132 of the syringe 110) is dispensed from the syringe 110 through the orifice 128. Accordingly, fluid on the distal side 144 of the knob 136 flows out from the syringe 110 through the orifice 128 and, if applicable, the needle, and fluid on the proximal side 142 of the knob 136 flows through the aperture(s) 140 in the knob 136 and then through the orifice 128 and, if applicable, the needle.

Contemporaneous with the dispensing of the fluid contained within the distal chamber 132, the second barrel 116, and therefore, the fluid in the chamber thereof (i.e., the proximal chamber 158 of the syringe 110) and the valve 120, continues to move toward the distal end 130 of the first barrel 112, and eventually, the valve 120 engages the knob 136 in the first barrel 112. More specifically, and with reference to FIG. 4, the valve 120 and the knob 136 are arranged such that plug 164 of the valve 120 is axially aligned with the knob 136. As the valve 120 engages the knob 136 and continues to move toward the distal end 130, the knob 136 dislodges the plug 164 from the valve base 160, thereby opening the valve 120 and allowing at least some of the fluid in the fluid chamber of the second barrel 116 (i.e., the proximal chamber 158 of the syringe 110) to flow out therefrom through the aperture 162 in the valve base 160. This fluid then flows through the aperture(s) 140 in the knob 136 and out of the syringe 110 through the orifice 128. As the base portion 160 of the valve 120, and thus, the second barrel 116, continues to move toward the distal end 130 of the first barrel 112 without the plug 164, it passes over at least a portion of the knob 136 (i.e., at least a portion of the knob 136 passes through the aperture 162 in the valve base 160) such that the knob 136 is now disposed within the proximal chamber 158 of the syringe 110. As a result, the remaining fluid contained in the proximal chamber 158 may then pass through the aperture(s) 140 in the knob 136 and out of the syringe 110 through the orifice 128 and, if applicable, the needle. The flow of fluid out of the proximal chamber 158 is promoted or advanced by continued force applied to the plunger 122, which urges the fluid out from the proximal chamber 158 as the plunger 122 continues to move within the interior space 118 of the second barrel 116 toward the distal end 148 thereof.

It will be appreciated that in an embodiment, all of the fluid in the distal chamber 132 of the syringe 110 will have been dispensed from the syringe 110 prior to the plug 164 being dislodged from the valve base 160 of the valve and the fluid in the proximal chamber 158 being dispensed from the syringe 110 such that the fluids in the respective chambers do not mix. In other embodiments, most, if not all, of the fluid in the distal chamber 132 will have been dispensed from the syringe 110 prior to the plug 164 being dislodged and the fluid in the proximal chamber 158 being dispensed in order to substantially limit, if not prevent, the fluid in the proximal chamber 158 mixing with the fluid in the distal chamber 132.

With reference to FIGS. 5-8, there is shown a diagrammatic representation of another embodiment of the syringe 110 (i.e., syringe 110'). This embodiment and that of FIGS. 3 and 4 are similar in many respects, and as such, similar components and their descriptions may not necessarily be repeated here. Additionally, to the extent components in this embodiment differ from those in the embodiment illustrated in FIGS. 3 and 4, reference numerals for those differing components have a "prime" symbol (i.e., 110' rather than 110) added thereto. In any event, in at least some embodiments, the syringe 110' comprises a partially-loaded syringe having one or more fluid chambers that are pre-loaded or pre-filled and one or more empty or fillable chambers that may be filled by a user rather than the manufacturer.

As with the embodiment illustrated in FIGS. 3 and 4, in this embodiment, when the first barrel 112 is assembled with second barrel 116 (i.e., barrel 116' in FIGS. 5 and 6), at least a portion of the interior space 114 of the first barrel 112 proximate the distal end 130 thereof comprises a fluid chamber that comprises the distal chamber 132 of the syringe 110'. In an embodiment, the chamber 132 may initially be empty or fillable when the syringe is provided to a customer, for example, a health care practitioner, to allow the customer to aspirate or fill the chamber 132 with a fluid (e.g., drug) of his/her choosing. Similarly, when the first barrel 112 is assembled with the second barrel 116', at least a portion of the interior space 118 of the second barrel 116' proximate the distal end 148 thereof comprises a fluid chamber that comprises the proximal chamber 158 of the syringe 110'. However, unlike the distal chamber 132, the proximal chamber 158 may be pre-loaded or pre-filled with a particular fluid (e.g., saline) by the syringe manufacturer or otherwise prior to delivery of the syringe 110' to a customer.

Figure 7:
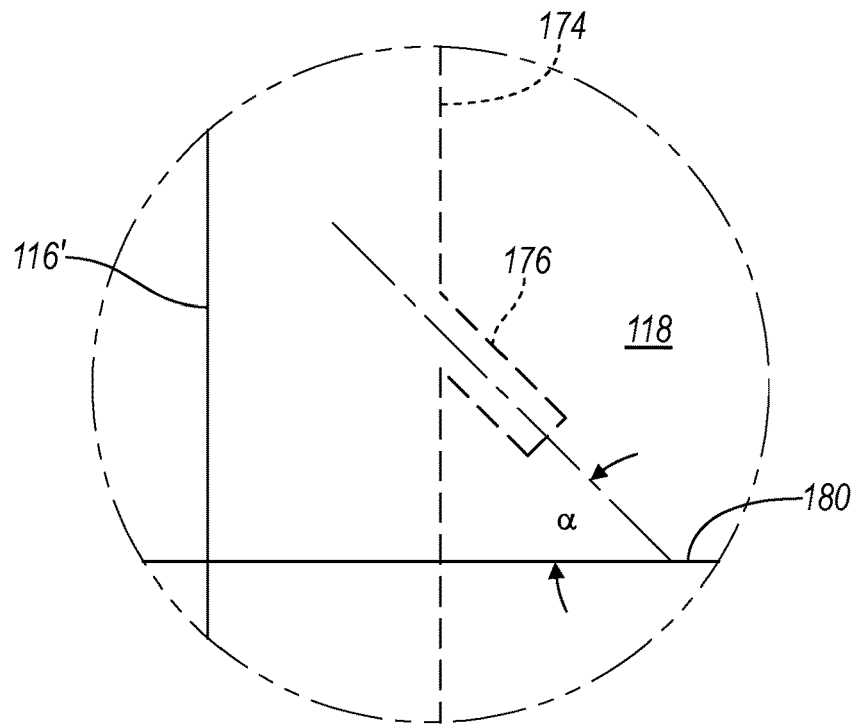
FIG. 7 is an enlarged view of a portion of a second or inner barrel of the syringe illustrated in FIG. 5 showing an engagement member of the second barrel.

Unlike the embodiment illustrated in FIGS. 3 and 4, the second barrel 116' in the embodiment illustrated in FIGS. 5-7 comprises one or more engagement members 176 extending into the interior space 118 of the second barrel 116' from one or more inner surfaces 174 thereof. As will be described in greater detail below, the engagement member(s) 176 are configured for engagement with complementary engagement members 178 of the plunger 122 of the syringe 110' (i.e., plunger 122'), and the respective engagement members 176, 178 of the barrel 116' and the plunger 122' are configured such that movement of the plunger 122' relative to the second barrel 116' in a first axial direction (i.e., toward the proximal end 146 of the second barrel 116') is limited or restricted by the engagement members, while movement of the plunger 122' relative to the second barrel 116' in a second axial direction (i.e., away from the proximal end 146 of the second barrel 116' and toward the distal end 148 of the second barrel 116') is effectively unlimited or unrestricted by the engagement members.

As shown, for example, in FIG. 7, in an embodiment, the engagement member(s) 176 of the second barrel 116' comprise one or more projections (e.g., tabs, barbs, etc.), at least a portion of each of which projects from an inner surface 174 of the second barrel 116' in both an axial and radially-inward direction toward the distal end 148 of the second barrel 116'. Accordingly, in an embodiment, at least a portion of each of the projection(s) (i.e., projection(s) 176) projects into the interior space 118 of the barrel 116' and toward the distal end 148 thereof at an acute angle α relative to a horizontal plane 180 that is perpendicular to the axis E of the second barrel 116', and in an illustrative embodiment, at a non-zero acute angle. While a particular embodiment of an engagement member 176 has been described, it will be appreciated that other suitable engagement members may certainly be used, as the present disclosure is not intended to be limited to any particular type of engagement member(s). In any event, in an embodiment—and for reasons that will be appreciated in view of the description below—the engagement member(s) 176 may be elastically deformable or resilient.

In an embodiment, the second barrel 116' includes a single engagement member/projection 176. In other embodiments, however, the second barrel 116' includes a plurality of engagement members/projections 176 that may be arranged in any number of patterns or ways. For example, in an embodiment, the second barrel 116' includes a plurality of engagement members 176 spaced (equally or unequally, depending on the implementation) about the perimeter of the interior space 118 of the second barrel 116' (e.g., circumferentially spaced about the inner surface 174 of the second barrel 116' in an embodiment wherein the second barrel has a cylindrical shape) and disposed within a common horizontal plane that is perpendicular to the axis E (i.e., the engagement members 176 are all located the same distance from the opening 154 at the proximal end 146 of the second barrel 116'). In another embodiment, the second barrel 116' may include a plurality of engagement members 176 that again are spaced either equally or unequally about the perimeter of the interior space 118 of the second barrel 116', but in this embodiment, one or more of engagement members 176 may be disposed within a different horizontal plane than that in which one or more of the other engagement members 176 is/are disposed. In yet another embodiment, the second barrel 116' may include a plurality of engagement members 176 divided into a number of subsets. For each subset, the engagement members 176 thereof may be spaced about the perimeter of the interior space 118 and disposed within a common horizontal plane that is different than the horizontal plane(s) in which the engagement member(s) 176 of the other subsets is/are disposed (e.g., the engagement members 176 of one subset may be disposed in a horizontal plane that is axially spaced from the horizontal plane(s) in which the engagement members 176 of other subsets are disposed). Accordingly, it will be appreciated that any number of engagement members 176 and arrangements/patterns thereof may be used, as the present disclosure is not intended to be limited to any particular number of engagement member(s) or arrangement(s) thereof.

As with the embodiment illustrated in FIGS. 3 and 4, when the syringe 110' is assembled, the plunger 122' is carried within the interior space 118 of the second barrel 116', and is operative to cause fluid in the syringe 110' to be dispensed therefrom. The plunger 122' may also comprise an elongate shaft 166 having a first end 168 and a second end 170 opposite the first end 168, and an axis F extending between and through the first and second ends 168, 170. The plunger 122' is also sized and shaped such that it may be inserted into the interior space 118 of the second barrel 116' through the opening 154 at the proximal end 146 thereof. The plunger 122' may further include a stopper 172 (i.e., stopper 172') coupled to and/or carried by the elongate shaft 166 at the second end 170 thereof. As with the embodiment illustrated in FIGS. 3 and 4, the stopper 172' provides a liquid seal to prevent fluid in the fluid chamber of the second barrel 116' (i.e., the proximal chamber 158 of the syringe 110') from flowing past the stopper 172' and potentially out of the syringe 110' through the opening 154 at the proximal end 146 of the second barrel 116'. To that end, in an embodiment, at least a portion of the stopper 172' is sufficiently elastically deformable or resilient (e.g., formed of rubber, plastic, or another suitable material) such that it may be compressed for insertion into the interior space 118 of the second barrel 116', and then upon insertion, returns at least partially to its original form and applies a radial force against one or more interior surface(s) 174 of the second barrel 116'. In addition to providing a seal, the stopper 172' also serves to wipe one or more interior surface(s) 174 of the second barrel 116' as the plunger 122' is depressed and moves along the length of the second barrel 116' in either axial direction relative to the axis E of the second barrel in order to, for example, maximize the amount of fluid that is dispensed from the syringe 110'.

Unlike the embodiment illustrated in FIGS. 3 and 4, however, the plunger 122' in the embodiment illustrated in FIGS. 5-8 comprises one or more engagement members 178 that are complementary to and configured for engagement with the one or more engagement members 176 of the second barrel 116'. Again, and as will be described in greater detail below, the respective engagement members 176, 178 of the barrel 116' and the plunger 122' are configured such that movement of the plunger 122' relative to the second barrel 116' in a first axial direction (i.e., toward the proximal end 146 of the second barrel 116') is limited or restricted by the engagement members, while movement of the plunger 122' relative to the second barrel 116' in a second axial direction (i.e., away from the proximal end 146 of the second barrel 116' and toward the distal end 148 of the second barrel 116') is effectively unlimited or unrestricted by the engagement members.

Figure 8:
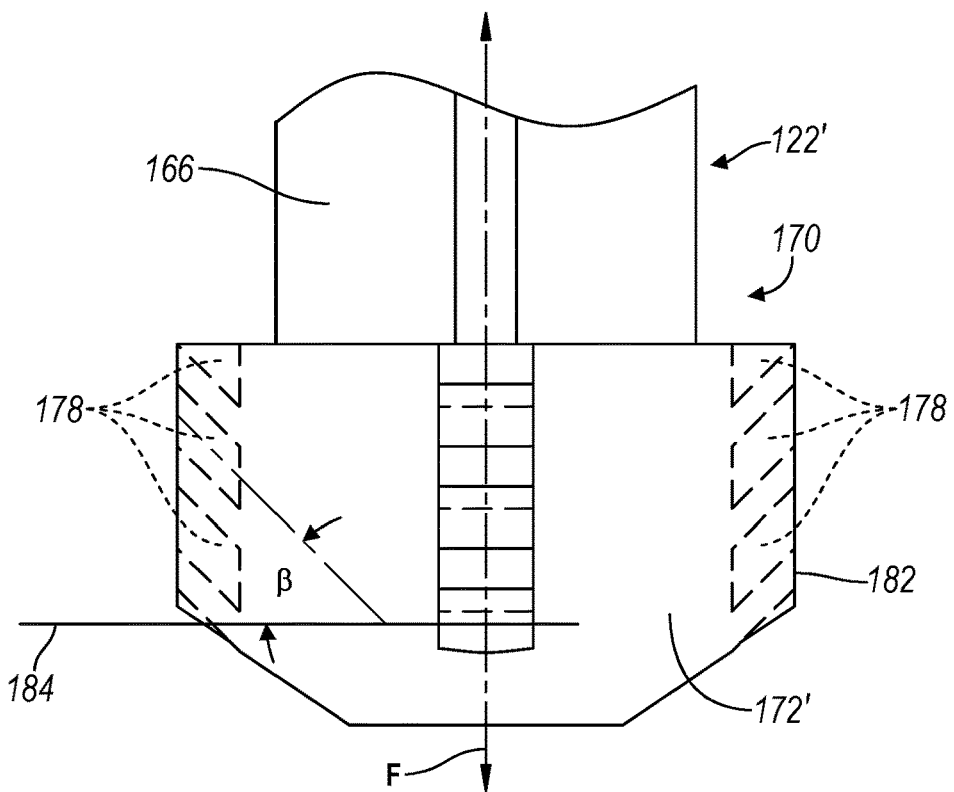
FIG. 8 is a diagrammatic and elevation view of a portion of a plunger of the syringe illustrated in FIG. 6 showing a stopper and a plurality of engagement features of the plunger.

As shown, for example, in FIGS. 6 and 8, in an embodiment, the engagement member(s) 178 of the plunger 122' comprise one or more voids (e.g., slots, recesses, etc.) in the stopper 172' of the plunger 122'. In an embodiment, at least a portion of each of the voids (i.e., void(s) 178) extends into the stopper 172' from an outer surface 182 thereof in both an axial and radially-inward direction away from the shaft 166 of the plunger 172', and when assembled with the second barrel 116', toward the distal end 148 of the second barrel 116'. Accordingly, in an embodiment and as best shown in FIG. 8, at least a portion of each of the void(s) 178 extends at an acute angle β relative to a horizontal plane 184 that is perpendicular to the axis F of the plunger 122', and in an illustrative embodiment, at a non-zero acute angle.

In an embodiment, the plunger 122' includes a single engagement member/void 178; in other embodiments, however, the plunger 122' includes a plurality of engagement members/voids 178. For example, in an embodiment, the plunger includes a plurality of engagement members 178 that are spaced (equally, in an embodiment, and unequally, in another embodiment) about the perimeter of the stopper 172' (e.g., circumferentially spaced about the stopper in an embodiment wherein the stopper has a cylindrical shape) and that are disposed within a common horizontal plane that is perpendicular to the axis F of the plunger 122' (i.e., the engagement members 178 are all located the same distance from the first end 168 of the elongate shaft 166). In another embodiment, the plunger 122' may include a plurality of engagement members 178 that again are spaced either equally or unequally about the perimeter of the stopper 172', but in this embodiment, one or more of engagement members may be disposed within a horizontal plane that is different than that in which one or more of the other engagement members 178 is/are disposed. In yet another embodiment, the plunger 122' may include a plurality of engagement members 178 divided into a number of subsets. For each subset, the engagement members 178 thereof may be spaced about the perimeter of the stopper 172' and disposed within a common horizontal plane that is different than the horizontal plane(s) in which the engagement member(s) 178 of the other subsets is/are disposed (e.g., the engagement members 178 of one subset may be disposed in a horizontal plane that is axially spaced from the horizontal plane(s) in which the engagement members 178 of other subsets are disposed). In an embodiment, the arrangement or pattern of the engagement members 178 mirrors that of the engagement members 176 of the second barrel 116; while in other embodiments, the arrangements or patterns of the respective engagement members 176, 178 may be at least partially different.

Accordingly, it will be appreciated in view of the foregoing that any number of engagement members 178 and arrangements/patterns thereof may be used, as the present disclosure is not intended to be limited to any particular number of engagement member(s) or arrangement(s) thereof. Additionally, while the description above has been with respect to the engagement members 178 being associated with the stopper 172' of the syringe 110', it other embodiments, the engagement members 178 may be associated with a different portion of the plunger 122' (e.g., the shaft 166 of the plunger 122'), and such embodiments remain within the spirit and scope of the present disclosure.

With particular reference to FIGS. 5 and 6, operation of the syringe 110' will now be described. In an instance wherein the chamber of the first barrel (i.e., the distal chamber 132) is initially empty, the syringe 110' may be operated to fill the chamber 132. To do so, the plunger 122' is pulled in an axial direction toward the proximal ends 126, 146 of the first and second barrels 112, 116', respectively (i.e., away from the fluid chambers in the first and second barrels 112, 116'). As the plunger 122' is pulled, it moves or slides within the interior space 118 of the second barrel 116'. As the plunger 122' moves, one or more of the engagement members 176 of the second barrel 116' becomes engaged with one or more engagement members 178 of the plunger 122' (e.g., in the stopper 172'). In an embodiment, this comprises the one or more engagement members 176 of the second barrel 116' (e.g., projections) being inserted into and captured within the one or more engagement members 178 (e.g., void(s)) of the stopper 172'. As a result, as the plunger 122' is pulled further in the axial direction, the second barrel 116' moves along with the plunger 122' in the same axial direction. As the second barrel 116' moves, fluid may be aspirated into the distal chamber 132 of the syringe 110' from, for example, a vile, thereby filling the distal chamber 132 of the syringe 110'.

Once the distal chamber 132 has been filled, the syringe 110' may be operated to dispense the fluid in both the distal and proximal chambers 132, 158. To do so, the plunger 122' is depressed in an axial direction toward the distal end 148 of the second barrel 116' (i.e., toward the fluid in the fluid chamber thereof). The pressure applied to the plunger 122' is transferred to the fluid in the proximal chamber 158 by virtue of the stopper 172' being in contact with the fluid. This causes a number of things to happen. First, the pressure or force exerted on the plunger 122' causes the second barrel 116' to move in an axial direction toward the distal end 130 of the first barrel 112. As a result, fluid in the fluid chamber of the first barrel 112 (i.e., the distal chamber 132 of the syringe 110') is dispensed or flows from the syringe 110' through the orifice 128. Accordingly, fluid on the distal side 144 of the knob 136 flows out from the syringe 110' through the orifice 128 and, if applicable, the needle, and fluid on the proximal side 142 of the knob 136 flows through the aperture(s) 140 in the knob 136 and then through the orifice 128 and, if applicable, the needle.

Contemporaneous with the dispensing of the fluid contained within the distal chamber 132, the second barrel 116', and therefore, the fluid in the chamber 158 and the valve 120, continues to move toward the distal end 130 of the first barrel 112, and eventually, the valve 120 engages the knob 136 in the first barrel 112. More specifically, and with reference to FIG. 6, the valve 120 and the knob 136 are arranged such that the plug 164 of the valve 120 is axially aligned with the knob 136. As the valve 120 engages the knob 136 and continues to move toward the distal end 130, the knob 136 dislodges the plug 164 from the valve base 160, thereby opening the valve 120 and allowing at least some of the fluid in the fluid chamber of the second barrel 116' (i.e., the proximal chamber 158 of the syringe 110') to flow out therefrom through the aperture 162 in the valve base 160. This fluid then flows through the aperture(s) 140 in the knob 136 and out of the syringe 110' through the orifice 128 and, if applicable, the needle. After the valve 120 is "opened" and fluid begins flowing out from the chamber of the second barrel 116' (i.e., the proximal chamber 158), the continued depressing of the plunger 122' causes the plunger 122' to move relative to the second barrel 116' within the interior space 118 of the second barrel 116'. As a result, the engagement members 176, 178 of the second barrel 116' and that or those of the plunger 122' that were previously engaged become disengaged (i.e., the engagement member(s) or protrusion(s) 176 of the second barrel 116' exit(s) the engagement member(s) or void(s) 178 of the plunger 172'). This movement of the plunger 122' relative to the second barrel 116' forces the fluid to flow out from the proximal chamber 158. As the plunger 122' is urged further toward the distal end 148 of the second barrel 116', engagement member(s) 176 of the second barrel 116' that are located distally of the stopper 172' are sufficiently resilient or elastically deformable to allow the plunger 122', and the stopper 172' thereof, in particular, to pass by without engaging engagement member(s) 178 of the plunger 122'. More specifically, the engagement member(s) 176 are configured such that they compress as they are passed over by the stopper as it moves toward the distal end 148 of the second barrel 116', and then return.

As the base portion 160 of the valve 120, and thus, the second barrel 116', continues to move toward the distal end 130 of the first barrel 112 without the plug 164, it passes over at least a portion of the knob 136 (i.e., at least a portion of the knob 136 passes through the aperture 162 in the valve base 160) such that the knob 136 is now disposed within the proximal chamber 158 of the syringe 110'. As a result, the remaining fluid contained in the proximal chamber 158 may then pass through the aperture(s) 140 in the knob 136 and out of the syringe 110' through the orifice 128 and, if applicable, the needle. As described above, the flow of fluid out of the proximal chamber 158 is promoted or advanced by continued force applied to the plunger 122', which urges the fluid out from the proximal chamber 158 as the plunger 122' continues to move within the interior space 118 of the second barrel 116' toward the distal end 148 thereof and applies a force to the fluid in the chamber 158.

It will be appreciated that in an embodiment, all of the fluid in the distal chamber 132 of the syringe 110' will have been dispensed from the syringe prior to the plug 164 being dislodged from the valve base 160 and the fluid in the proximal chamber 158 being dispensed, such that the fluids in the distal and proximal chambers 132, 158 do not mix. In other embodiments, most, if not all, of the fluid in the distal chamber 132 will have been dispensed from the syringe 110' prior to the plug 164 being dislodged from the valve base 160 and the fluid in the proximal chamber 158 being dispensed in order to substantially limit, if not prevent, the fluid in the proximal chamber 158 mixing with the fluid in the distal chamber 132.

As was described above, engagement member(s) 176 of the second barrel 116' are sufficiently resilient or elastically deformable to allow the plunger 122', and the stopper 172' thereof in particular, to pass by without engaging engagement member(s) 178 of the plunger 122' when moving in an axial direction toward the distal end 148 of the second barrel 116'. More specifically, the engagement member(s) 176 of the second barrel 116' are configured such that they compress as the stopper 172' passes over as it moves toward the distal end 148 of the second barrel 116', and then return to their original state after the stopper 172' clears that or those members 176. Accordingly, the engagement member(s) 176 of the second barrel 116' do not impede the movement of the plunger 122' in an axial direction toward the distal end 148 of the second barrel 116'.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A multi-chamber, sequential-delivery syringe, comprising:
   a first fluid chamber,
   a second fluid chamber;
   a valve disposed between the first and second fluid chambers, the valve having a base portion and a plug, the base portion defining an aperture therethrough, the valve having a first state with the plug covering the aperture to form a seal between the first and second fluid chambers, and the valve having a second state with the plug spaced apart from the base portion to allow fluid in the second fluid chamber to flow out from the second fluid chamber via the aperture;
   a plunger configured to be carried within the second fluid chamber and configured for movement within the second fluid chamber; and a knob disposed within the first fluid chamber and having one or more apertures therein configured to allow fluid to flow therethrough;
wherein the knob and valve are arranged such that the knob is configured to open the valve and place the valve in the second state when the valve engages the knob, thereby allowing fluid in the second fluid chamber to be dispensed from the syringe subsequent to fluid in the first fluid chamber being dispensed from the syringe; and
wherein the aperture of the base portion is sized to receive the knob therethrough such that at least a portion of the knob is configured to pass through the aperture in the base portion such that the knob is disposed within the second chamber when the valve is in the second state.

2. The syringe of claim 1, wherein the knob forms a first curved, convex surface that projects towards the second fluid chamber;
wherein the plug forms a second curved convex surface that projects towards the first fluid chamber; and
wherein the first and second curved convex surfaces contact one another when the valve is in the second state.

3. The syringe of claim 1, wherein the knob has a plurality of apertures therein configured to allow fluid flow therethrough.

4. A multi-chamber, sequential-delivery syringe, comprising:
a hollow barrel having
a proximal end, a distal end, and an axis extending therebetween,
an interior surface of the hollow barrel defining an interior space extending at least partially between the proximal and distal ends of the hollow barrel, and
a knob proximate the distal end of the hollow barrel and in direct contact with the interior surface of the hollow barrel, the knob projecting into the interior space of the hollow barrel in an axial direction toward the proximal end of the hollow barrel, the knob having one or more apertures therein configured to allow fluid to flow therethrough;
a plunger carried by the hollow barrel and configured for movement within the interior space of the hollow barrel, the plunger in direct contact with the interior surface of the hollow barrel; and
a valve carried within the hollow barrel and disposed between the plunger and the knob in the interior space of the hollow barrel, the valve dividing the interior space of the hollow barrel into a proximal chamber between the plunger and the valve, and a distal chamber between the valve and the distal end of the hollow barrel, wherein the valve is in direct contact with the interior surface of the hollow barrel and is configured for movement within the interior space of hollow barrel as the plunger moves;
wherein the knob and valve are arranged such that the knob is configured to open the valve when the valve engages the knob, thereby allowing fluid in the proximal chamber to be dispensed from the syringe subsequent to fluid in the distal chamber being dispensed from the syringe.

5. The syringe of claim 4, wherein the proximal chamber is at least partially defined by the interior surface of the hollow barrel such that fluid within the proximal chamber contacts the interior surface of the hollow barrel; and
wherein the distal chamber is at least partially defined by the interior surface of the hollow barrel such that fluid within the distal chamber contacts the interior surface of the hollow barrel.

6. The syringe of claim 4, wherein the valve has a base portion and a plug, the base portion having an outer edge in contact with the interior surface of the hollow barrel and configured for movement within the interior space of the hollow barrel as the plunger moves, the base portion defining an aperture therethrough, the aperture of the base portion being axially aligned with the knob, the plug being carried by the base portion and configured to cover the aperture of the base portion to prevent fluid flow therethrough, wherein the knob engages the plug to dislodge the plug from the base portion for fluid flow through the valve.

7. The syringe of claim 6, wherein the aperture of the base portion of the valve is sized to receive at least a portion of the knob therethrough such that the at least a portion of the knob is positioned on a proximal side of the base portion.

8. A multi-chamber, sequential-delivery syringe, comprising:
a first hollow barrel having
a proximal end, a distal end, and an axis extending therebetween,
an interior space extending a least partially between the proximal and distal ends of the first hollow barrel, and
a knob proximate the distal end of the first hollow barrel and projecting into the interior space of the first hollow barrel in an axial direction toward the proximal end of the first hollow barrel, the knob having one or more apertures therein configured to allow fluid to flow therethrough;
a second hollow barrel configured to be carried by the first hollow barrel and having
a proximal end, a distal end, and an axis extending therebetween that is coaxial with the axis of the first hollow barrel,
an interior space extending a least partially between the proximal and distal ends of the second hollow barrel, and
a valve disposed at the distal end of the second hollow barrel, the valve having a base portion and a plug, the base portion defining an aperture therethrough, the plug covering the aperture to prevent fluid flow through the valve when the valve is in a closed state,
wherein at least a portion of the second hollow barrel is disposed and configured to move within the interior space of the first hollow barrel;
a plunger configured to be carried by the second hollow barrel and configured for movement within the interior space of the second hollow barrel;
a distal fluid chamber comprising a portion of the interior space of the first hollow barrel and extending between the distal end of the second hollow barrel and the distal end of the first hollow barrel; and
a proximal fluid chamber comprising a portion of the interior space of the second hollow barrel and extending between the plunger and the distal end of the second hollow barrel;
wherein the knob of the first hollow barrel and the valve of the second hollow barrel are arranged such that the knob is configured to open the valve when the plug of the valve engages the knob, thereby allowing fluid in the proximal chamber to be dispensed from the syringe subsequent to fluid in the distal chamber being dispensed from the syringe; and wherein the aperture of the base portion is sized to receive the knob therethrough such that at least a portion of the knob is configured to pass through the aperture in the base portion when the valve is in an open state such that the knob is disposed within the proximal fluid chamber in the interior space of the second hollow barrel and the plug is spaced apart from the aperture.

9. The syringe of claim 8, wherein the knob forms a first curved, convex surface that projects towards the proximal end of the first hollow barrel;
    wherein the plug forms a second curved convex surface that projects towards the distal end of the first hollow barrel; and
    wherein the first and second curved convex surfaces contact one another when the valve is open.

10. The syringe of claim 8, wherein the knob has a plurality of apertures therein configured to allow fluid flow therethrough.

11. A multi-chamber, sequential-delivery syringe, comprising:
    a first hollow barrel having
        a proximal end, a distal end, and an axis extending therebetween, and
        an interior space extending at least partially between the proximal and distal ends of the first hollow barrel,
    a second hollow barrel configured to be carried by the first hollow barrel and having
        a proximal end, a distal end, and an axis extending therebetween that is coaxial with the axis of the first hollow barrel,
        an interior space extending at least partially between the proximal and distal ends of the second hollow barrel,
        a valve disposed at the distal end of the second hollow barrel, and
        one or more first engagement members each projecting from an inner surface of the second hollow barrel into the interior space of the second hollow barrel in both an axially and radially-inwardly direction toward the distal end of the second hollow barrel relative to the axis of the second hollow barrel,
        wherein at least a portion of the second hollow barrel is disposed within the interior space of the first hollow barrel and further wherein the second hollow barrel is configured to move within the interior space of the first hollow barrel;
    a plunger configured to be carried by the second hollow barrel and for movement within the interior space of the second hollow barrel, wherein the plunger includes one or more second engagement members that are complementary to and configured for engagement with the first engagement members of the second hollow barrel;
    wherein the one or more second engagement members directly engage the one or more first engagement members when the plunger is moved in an axial direction toward the proximal end of the second hollow barrel to limit the axial movement of the plunger relative to the second hollow barrel such that the plunger and the second hollow barrel move together towards the proximal end of the first hollow barrel; and
    wherein, when the plunger is moved in an axial direction toward the distal end of the second hollow barrel, the one or more second engagement members are axially aligned with the one or more first engagement members without directly engaging the one or more first engagement members such that movement of the plunger relative to the second barrel in the axial direction toward the distal end of the second hollow barrel is unrestricted by the first and second engagement members;
    a fillable distal fluid chamber comprising a portion of the interior space of the first hollow barrel and extending between the distal end of the second hollow barrel and the distal end of the first hollow barrel; and
    a proximal fluid chamber comprising a portion of the interior space of the second hollow barrel and extending between the plunger and the distal end of the second hollow barrel.

12. The syringe of claim 11, wherein the first hollow barrel further comprises a knob proximate the distal end of the first hollow barrel projecting into the interior space of the first hollow barrel in an axial direction toward the proximal end of the first hollow barrel, the knob having one or more apertures therein configured to allow fluid to flow therethrough, and further wherein the knob and the valve of the second hollow barrel are arranged such that the knob is configured to open the valve when the valve engages the knob, thereby allowing fluid in the proximal fluid chamber to be dispensed from the syringe subsequent to fluid in the distal fluid chamber being dispensed from the syringe.

13. The syringe of claim 11 wherein the one or more first engagement members are elastically deformable to compress and then return as the plunger and the one or more second engagement members passes directly over the one or more first engagement members when the plunger is moved in the axial direction toward the distal end of the second hollow barrel.

14. The syringe of claim 11, wherein the one or more second engagement members of the plunger are positioned at the distal end of the plunger.

15. The syringe of claim 11, wherein the plunger has a stopper carried by the second hollow barrel for movement within the second barrel, wherein the stopper includes the one or more second engagement members that are complementary to and configured for engagement with the one or more first engagement members of the second hollow barrel.

16. The syringe of claim 11, wherein at least one of the one or more first engagement members are positioned within the proximal fluid chamber of the second hollow barrel.

17. The syringe of claim 11, wherein each of the one or more second engagement members is defined by a void extending into the plunger from an outer surface of the plunger in both an axial and radially-inward direction toward the distal end of the second hollow barrel.

18. The syringe of claim 17, wherein each of the one or more first engagement members is defined by a projection.

* * * * *